United States Patent
Bandyopadhyay et al.

(12) 
(10) Patent No.: US 6,197,535 B1
(45) Date of Patent: Mar. 6, 2001

(54) METHODS FOR PURIFYING AND ASSAYING A CONUS γ-CARBOXYLASE

(75) Inventors: Pradip K. Bandyopadhyay; Craig S. Walker; Baldomero M. Olivera, all of Salt Lake City, UT (US)

(73) Assignee: University of Utah Research Foundation, Salt Lake City, UT (US)

( * ) Notice: Subject to any disclaimer, the term of this patent is extended or adjusted under 35 U.S.C. 154(b) by 0 days.

(21) Appl. No.: 09/247,527

(22) Filed: Feb. 10, 1999

Related U.S. Application Data (60) Provisional application No. 60/074,204, filed on Feb. 10, 1998.

(51) Int. Cl.$^7$ .............................. C12Q 1/48; C12N 9/10
(52) U.S. Cl. .............................................. 435/15; 435/193
(58) Field of Search ....................... 435/193, 15

(56) References Cited

U.S. PATENT DOCUMENTS

| | | | |
|---|---|---|---|
| 5,830,998 | 11/1998 | Maccecchini | 530/326 |
| 5,854,217 | 12/1998 | Maccecchini | 514/13 |

FOREIGN PATENT DOCUMENTS

| | | |
|---|---|---|
| 9820026 | 5/1998 | (WO) . |
| 9831705 | 7/1998 | (WO) . |

OTHER PUBLICATIONS

Gray, W.R. and Olivera, B.M. (1988). "Peptide Toxins from Venomous *Conus*Snails." *Ann. Rev. Biochem.* 57:665–700.

Bandyopadhyay, P.K. et al. (1998). "Conantokin–G Precursor and Its Role in γCarboxylation by a Vitamin K–dependent Carboxylase from a *Conus*Snail." *J. Biol. Chem.* 273:5447–5450.

Czerwiec et al., "Vitamin K–dependent Carboxylase: Comparison of the Bovine Gamma–Carboxylase with the Gamma–Carboxylase from the Marine Cone Snail", Blood, (1996) vol. 88, No. 10 Suppl. 1 Part 1–2, p. 523A, Abstract 2079, Dec. 1996.*

Stanley et al., "Identification of a Vitamin K–dependent Carboxylase in the Venom Duct of a Conus Snail", FEBS Letters, vol. 407, No. 1, pp. 85–88, Apr. 1997.*

Bush et al., "Hydrophobic Amino Acids Define the Carboxylation Recognition Site in the Precursor of the Gamma–Carboxyglutamic–Acid–Containing Conotoxin Epsilon–TxIX from the Marine Cone Snail Conus Textile", Biochemistry, vol. 38, No. 44, pp. 14660–14666, SciSearch Abst AN 1999:888719, Nov. 1999.*

* cited by examiner

*Primary Examiner*—Jon P. Weber
(74) *Attorney, Agent, or Firm*—Rothwell, Figg, Ernst & Manbeck, p.C.

(57) ABSTRACT

The present invention is relates to a method for purifying a γ-carboxylase from Conus snails and to a method for assaying the activity of this γ-glutamyl carboxylase.

7 Claims, 4 Drawing Sheets

```
1/1                                  31/11
ATG CAC CTG TAC ACG TAT CTG TAT CTG CTG GTG CCC CTG GTG ACC TTC CAC CTA ATC CTA
 M   H   L   Y   T   Y   L   Y   L   L   V   P   L   V   T   F   H   L   I   L
61/21                                91/31
GGC ACG GGC ACA CTA GAT GAT GGA GGC GCA CTG ACT GAA CGC CGT TCA GCT GAC GCC ACA
 G   T   G   T   L   D   D   G   G   A   L   T   E   R   R   S   A   D   A   T
121/41                               151/51
GCG CTG AAA GCT GAG CCT GTC CTC CTG CAG AAA TCC GCT GCC CGC AGC ACC GAC GAC AAT
 A   L   K   A   E   P   V   L   L   Q   K   S   A   A   R   S   T   D   D   N
181/61                               211/71
GGC AAG GAC AGG TTG ACT CAG ATG AAG AGG ATT CTC AAA CAG CGA GGA AAC AAA GCC AGA
 G   K   D   R   L   T   Q   M   K   R   I   L   K   Q   R   G   N   K   A   R
241/81                               271/91
GGC GAA GAA GAA GTT CAA GAG AAT CAG GAA TTG ATC AGA GAA AAA AGT AAT GGA AAA AGA
 G   E   E   E   V   Q   E   N   Q   E   L   I   R   E   K   S   N   G   K   R
301/101
TAA
 *
```

FIG. 1a

```
      -80         -70         -60         -50         -40
       MHLYTYLYLLVPLVTFHLILGTGTLDDGGALTERRSADATALKAEPVLLQ
      -30         -20         -10    ↓    5       10        15        20
       KSAARSTDDNGKDRLTQMKRILKQRGNKARGEEEVQENQELIREKSNGKR
                                    │
                                    │   PROTEOLYTIC PROCESSING
                                    │
                                    │   POST-TRANSLATIONAL PROCESSING TO GLA
                                    │
                                    │   POST-TRANSLATIONAL AMIDATION
                                    ↓
                GEγγVQγNQγLIRγKSN#  CONANTOKIN G (L5V)

GEγγLQγNQγLIRγKSN#  CONANTOKIN G
```

METHODS FOR PURIFYING AND ASSAYING A CONUS γ-CARBOXYLASE

CROSS REFERENCE TO RELATED APPLICATION

The present application is related to U.S. provisional patent application Ser. No. 60/074,204 filed on Feb. 10, 1998, incorporated herein by reference.

BACKGROUND OF THE INVENTION

The present invention is relates to a method for purifying a γ-glutamyl carboxylase (also referred to herein as γ-carboxylase) from Conus snails and to a method for assaying the activity of this γ-carboxylase.

The publications and other materials used herein to illuminate the background of the invention, and in particular, cases to provide additional details respecting the practice, are incorporated by reference, and for convenience are referenced in the following text by number and are listed numerically in the appended List of References.

The vitamin K-dependent γ-carboxylation of glutamate residues was originally discovered as a novel post-translational modification in the blood coagulation cascade (1); some of the key clotting factors such as prothrombin must be γ-carboxylated in order for proper blood clotting to occur. Somewhat later, this post-translational modification was also found in certain bone proteins (2). This modification was restricted to these rather specialized mammalian systems until a very unusual peptide, conantokin-G, was described from the venom of the predatory marine snail, *Conus geographus* (3). Conantokin-G is a 17-amino acid peptide that inhibits the N-methyl-D-aspartate receptor (4). Unlike most Conus peptides, which are multiply disulfide-bonded, conantokin-G has no disulfide cross-links but has five residues of γ-carboxyglutamate residues; this remains the highest density of γ-carboxyglutamate found in any functional gene product characterized to date.

Most of the biologically active components of the Conus venom are multiply disulfide bonded peptides (the conotoxins). These have been shown to be initially translated as prepropeptide precursors, which are then post-translationally processed to yield the mature disulfide-crosslinked conotoxin. Conantokin-G differs strikingly from most conotoxins not only in having γ-carboxyglutamate residues, but also because it has no disulfide crosslinks. We report below an analysis of a cDNA clone encoding the conantokin-G precursor. Furthermore, we establish the probable function of one region of the precursor that is excised during the maturation of the functional conantokin-G peptide.

The presence of γ-carboxyglutamate in a non-mammalian system was initially controversial because vitamin K-dependent carboxylation of glutamate residues had primarily been thought to be a highly specialized mammalian innovation. However, we have found that conantokin-G is only one member of a family of peptides; a variety of other conantokins have been found including conantokin-T and conantokin-R from two other fish-hunting cone snails (5, 6). All three peptides have a high content of γ-carboxyglutamate (4–5 residues). γ-Glutamyl carboxylase has been purified from mammalian sources (7, 8) and has been expressed both in mammalian and insect cell lines (9, 10). Recently it was shown that, as is the case in the mammalian system, the carboxylation reaction in Conus venom ducts absolutely requires vitamin K, and the net carboxylation increases greatly in the presence of high concentrations of ammonium sulfate. In these respects, the mammalian and the Conus γ-carboxylation venom systems are very similar (11).

The propeptides of vitamin K-dependent blood coagulation proteins share extensive sequence similarity. This sequence is believed to interact with the carboxylase and constitutes the γ-carboxylation recognition sequence (γ-CRS). In this report, we analyze the conantokin-G precursor sequence for potential γ-CRS sequences. The results described below identify a sequence present in the −1 to −20 region of the conantokin-G prepropeptide which, when covalently linked to the N-terminal of the substrate enzyme, stimulates carboxylation by the Conus enzyme.

SUMMARY OF THE INVENTION

The present invention is relates to a method for purifying a γ-carboxylase from Conus snails and to a method for assaying the activity of this γ-carboxylase.

Figure 1A:
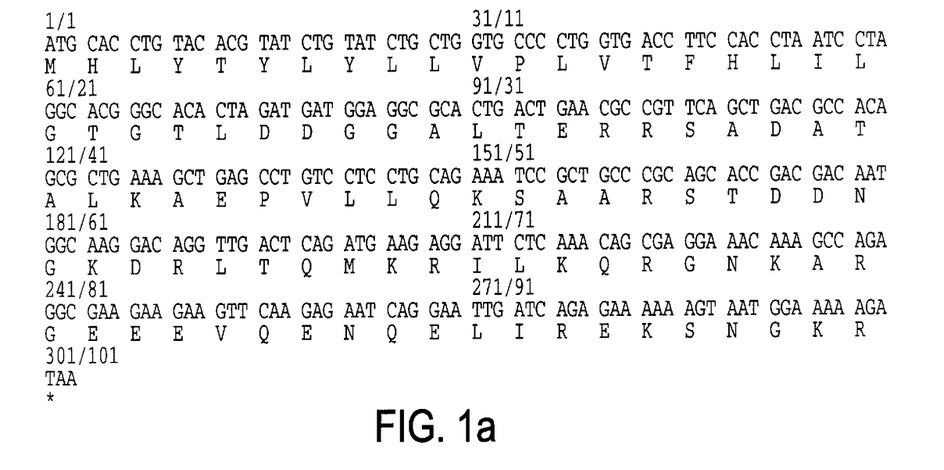

Conantokin-G isolated from the marine snail *Conus geographus* is a 17-amino acid γ-carboxyglutamate (Gla)-containing peptide that inhibits the N-methyl-D-aspartate receptor. We describe the cloning and sequence of conantokin-G cDNA and the possible role of the propeptide sequence. The cDNA encodes a 100-amino acid peptide. The N-terminal 80 amino acids constitute the prepro-sequence, and the mature peptide is derived from the remaining C-terminal residues after proteolysis, C-terminal amidation and a unique post-translational modification, γ-carboxylation of glutamate residues to Gla. Mature conantokin-G peptide containing Glu residues (E.Con-G) in place of Gla is a poor substrate for the vitamin K-dependent γ-glutamyl carboxylase (apparent $K_m$=3.4 mM). Using peptides corresponding to different segments of the propeptide, we investigated a potential role for the propeptide sequences in γ-carboxylation. Propeptide segment −20 to −1 covalently linked to E.Con-G or the synthetic pentapeptide FLEEL increased their apparent affinities two orders of magnitude. These substrates are not efficiently carboxylated by the bovine microsomal γ-glutamyl carboxylase, suggesting differences in specificities between the Conus and the mammalian enzyme. However, the role of propeptide in enhancing the efficiency of carboxylation is maintained. It has been found that the the Conus carboxylase properly carboxylates conantokin-G. That is, $Glu_2$ of conantokin-G is not carboxylated by the enzyme whereas $Glu_3$, $Glu_4$, $Glu_7$, $Glu_{10}$ and $Glu_{14}$ are carboxylated when the enzyme is added to the propeptide.

The −20 to −1 amino acid sequence of the prepropeptide is highly conserved among the conantokins. This region, or the entire prepropeptide, therefore can be used to prepare an affinity column to purify the carboxylase which post-translationally modifies Glu to γ-carboxyglutamate. Once the carboxylase is purified, it can be sequenced and cloned. In addition, the prepropeptide can be used to assay activity of the carboxylase from Conus.

BRIEF DESCRIPTION OF THE FIGURES

FIGS. 1A–B show the sequences of conantoking G. (FIG. 1A) Nucleotide sequence of cDNA of conantokin-G and the expected translation product, prepro-conantokin-G. The nucleotide sequence of FIG. 1A is SEQ ID NO:1 and the amino acid sequence is SEQ ID NO:2. (FIG. 1B) Sequence of prepro-conantokin-G (L5V) and the mature toxin sequence. The amino acid sequence of −80 to 20 shown in FIG. 1B is SEQ ID NO:2. Arrow shows expected proteolytic processing site for the release of mature toxin product. "γ" represents gamma-carboxyglutamate residues, and "#" indicates the amidated C-terminal residue. The initial cDNA isolated was of conantokin-G (L5V). The amino acid sequence for Conantokin G (L5V) shown in FIG. 1B is SEQ ID NO:3. We have since isolated conantokin-G coding-cDNA, which has a sequence identical to our initial isolate except for Leu instead of Val at position 5 of the mature toxin sequence. This sequence of Conantokin G shown in FIG. 1B is SEQ ID NO:4.

FIGS. 2A–B show a kinetic analysis of carboxylase activity using E.Con-G (FIG. 2A) and −20.Pro-E.Con.G as substrates (FIG. 2B). The data were fitted to a hyperbola in a single-site binding model. The apparent $K_m$ for E.Con-G was determined from a Lineweaver-Burk plot and for −20.Pro-E.Con-G from the best fit to a hyperbola.

FIG. 3 shows a kinetic analysis of the inhibition of carboxylation of −20.proE.Con-G by Pro(−20 to −1). The data were fitted to single site competitive binding model. 50 uM −20.Pro-E.Con-G was used in the carboxylation reaction and concentration of Pro(−20 to −1) was varied.

FIG. 4 shows the results of a gamma-carboxy-Glu (Gla) analysis of the reaction product from −20.pro.ConG carboxylation.

SUMMARY OF THE SEQUENCE LISTING

SEQ ID NO:1 is a DNA sequence encoding conantokin G (L5V) prepropeptide. SEQ ID NO:2 is the amino acid sequence for conantokin G (L5V) prepropeptide. SEQ ID NO:3 is the amino acid sequence for conantokin G (L5V). SEQ ID NO:4 is the amino acid sequence for conantokin G. SEQ ID NO:5 is the amino acid sequence of conantokin G propeptide. SEQ ID NO:6 is the amino acid sequence of human Factor IX propeptide. SEQ ID NO:7 is the amino acid sequence of human Factor X propeptide. SEQ ID NO:8 is the amino acid sequence of human prothrombin. SEQ ID NO:9 is C-terminus of conantokin G. SEQ ID NO:10 is the amino acid sequence of a test peptide. SEQ ID NO:11 is the amino acid sequence of E.Con-G. SEQ ID NO:12 is the amino acid sequence of −10.Pro-E.Con-G. SEQ ID NO:13 is the amino acid sequence of −20.Pro-E.Con-G. SEQ ID NO:14 is the amino acid sequence of −20.Pro-E.test peptide. SEQ ID NO:15 is the amino acid sequence of −20 to −1 of conantokin G prepropeptide. SEQ ID NO:16 is the amino acid sequence of −30 to −1 of conantokin G prepropeptide. SEQ ID NO:17 is the amino acid sequence of −40 to −21 of conantokin G prepropeptide. SEQ ID NO:18 is the amino acid sequence of −60 to −41 of conantokin G prepropeptide. SEQ ID NO:19 is the amino acid sequence of −20 to 6 of conantokin G prepropeptide. SEQ ID NO:20 is the amino acid sequence of −20 to −1 of conantokin G prepropeptide. SEQ ID NO:21 is the amino acid sequence of −20 to −1 of conantokin Oc prepropeptide. SEQ ID NO:22 is the amino acid sequence of −20 to −1 of conantokin R prepropeptide. SEQ ID NO:23 is the amino acid sequence of −20 to −1 of conantokin Sl prepropeptide. SEQ ID NO:24 is the amino acid sequence of −20 to −1 of conantokin L prepropeptide. SEQ ID NO:25 is the amino acid sequence of −20 to −1 of conantokin Gm prepropeptide. SEQ ID NO:26 is the amino acid sequence of −20 to −1 of conantokin Ca2 prepropeptide. SEQ ID NO:27 is the amino acid sequence of −20 to −1 of conantokin Qu prepropeptide. SEQ ID NO:28 is the consensus amino acid sequence of −20 to −1 of conantokin prepropeptides.

DETAILED DESCRIPTION OF THE INVENTION

The present invention is relates to a method for purifying a γ-carboxylase from Conus snails and to a method for assaying, the activity of this γ-carboxylase.

Conantokin-G isolated from the marine snail Conus geographus is a 17-amino acid γ-carboxyglutamate (Gla)-containing peptide that inhibits the N-methyl-D-aspartate receptor. We describe the cloning and sequence of conantokin-G cDNA and the possible role of the propeptide sequence. The cDNA encodes a 100-amino acid peptide. The N-terminal 80 amino acids constitute the prepro-sequence, and the mature peptide is derived from the remaining C-terminal residues after proteolysis, C-terminal amidation and a unique post-translational modification, γ-carboxylation of glutamate residues to Gla. Mature conantokin-G peptide containing Glu residues (E.Con-G) in place of Gla is a poor substrate for the vitamin K-dependent γ-glutamyl carboxylase (apparent $K_m$=3.4 mM). Using peptides corresponding to different segments of the propeptide, we investigated a potential role for the propeptide sequences in γ-carboxylation. Propeptide segment −20 to −1 covalently linked to E.Con-G or the synthetic pentapeptide FLEEL increased their apparent affinities two orders of magnitude. These substrates are not efficiently carboxylated by the bovine microsomal γ-glutamyl carboxylase, suggesting differences in specificities between the Conus and the mammalian enzyme. However, the role of propeptide in enhancing the efficiency of carboxylation is maintained.

We have demonstrated that γ-carboxylated 17-amino acid Conus peptide conantokin-G is initially translated as a prepropeptide of 100 amino acids. In general, the organization of the conantokin-G precursor is similar to that previously reported for disulfide-rich conotoxins from Conus venoms. The mature peptide is found in a single copy at the C-terminal end of the precursor. Before maturation of the peptide, a number of post-translational processing events have to take place (FIG. 1). These events include the γ-carboxylation of five glutamate residues, C-terminal amidation of asparagine-17 following excision of the C-terminal tripeptide, and a proteolytic event between $Arg^{-1}$ and $Gly^{1}$.

One notable feature of the conantokin-G prepropeptide is the length of the intervening region between the signal sequence and the mature peptide. The 59 amino acids in the intervening pro-region is the longest so far reported for any Conus venom peptide. We have demonstrated one potential function of this extended region: the presence of a γ-carboxylation recognition sequence for the Conus venom duct γ-glutamyl carboxylase in the −1 to −20 region.

In mammalian blood coagulation and bone Gla proteins, γ-carboxylation of glutamate residues is carried out by a vitamin K-dependent carboxylase. A conserved motif (16) γ-carboxylation recognition sequence in the propeptide sequence binds the γ-carboxylase and is required for a polypeptide substrate to be a high affinity target for the γ-carboxylase. In the experiments described above, we carried out an analysis using segments of the conantokin-G prepropeptide to identify potential sites that might serve as γ-carboxylase recognition signals for the Conus enzyme. The results reveal that a γ-carboxylation recognition sequence is included in the −1 to −20 region of the conantokin-G prepropeptide. This appears to increase the affinity of the Conus carboxylase by approximately two orders of magnitude under the assay conditions used.

Knobloch and Suttie (18) and others (19) found that the propeptide sequences of Factors IX and X at micromolar concentrations stimulated the carboxylation of oligopeptide substrates, suggesting a probable positive allosteric effector role. In addition, the propeptide at micromolar concentrations acted as a competitive inhibitor of carboxylation of a substrate whose sequences were based on residues −18 to +10 of prothrombin (20). Similarly, the Conus propeptide (−20 to −1) inhibits the carboxylation of propeptide-containing substrates, (i.e. −10.Pro-E.Con-G and −20.Pro.E.Con-G). However, we were unable to observe equivalent, strong stimulation of carboxylation of FLEEL and E.Con-G by the Conus propeptide.

The relevant propeptide sequence (−20 to −1) for conantokin-G, human Factors IX (21) and X (22), and prothrombin (23) are shown in Table 1.

TABLE I

Propeptide Sequences of γ-Carboxylated Conus and Mammalian Peptides

| Pro-Con-G | GKDRLTQMKRILKQRGNKAR | SEQ ID NO:5 |
|---|---|---|
| hFIX | TVFLDHENANKILNRPKR | SEQ ID NO:6 |
| hFx | SLFIRREQANNILARVTR | SEQ ID NO:7 |
| hPT | HVFLAPQQARSLLQRVRR | SEQ ID NO:8 |

Pro-Con-G is tbe propeptide sequence (−20 to −1) of conantokin-G; hFIX (21), hFX (22) and hPT (23) are the propeptide sequences of human Factors IX and X and prothrombin.

Except for the presence of a hydrophobic residue at position −16, the conantokin-G sequence does not appear to share the conserved features of the mammalian propeptides (16). Phenylalanine is present at position −16 in all of the propeptide sequences except in gas6 and protein S, in which it is leucine as in the case of Con-G. In addition, isoleucine is present at position −10 of Con-G in place of a conserved alanine residue. Besides, positions −6 and −7, which are always hydrophobic for the mammalian propeptide sequences, are basic and polar residues, respectively, for Con-G. This suggests differences between the recognition specificities of the mammalian and Conus enzymes. A preliminary characterization of the amino acids important for recognition by the Conus enzyme has been carried out. The individual basic amino acids in the propeptide region −20 to −1 can be replaced by alanine without significantly affecting the apparent $K_m$ for carboxylation. The importance of hydrophobic residues in the mammalian γ-CRS suggests that they may also be important for the Conus carboxylase, and this role needs to be investigated.

The orientation in which a Glu presents itself to the active site of the carboxylase may determine whether it will be carboxylated. In the case of Con-G not all the Glu residues are γ-carboxylated ($Glu^2$ is not carboxylated, whereas $Glu^3$ and $Glu^4$ are carboxylated). The solution structures of Con-C and Con-T as determined by CD and NMR spectroscopy (24, 25) are a mixture of α and $3_{10}$ helices. Rigby et al. (26) also determined the structure of the metal-free conformer of conantokin-G by NMR spectroscopy. In all of these structures, the Gla residues are on the same side of the conantokin structure; this would allow a membrane-bound enzyme to carry out efficient carboxylation of Glu residues oriented in the same direction with optimum stereochemistry.

In the discussion above, we have emphasized the differences in the γ-carboxylation recognition signal sequences in the mammalian and Conus systems. These differences may be due to the large evolutionary distance between the two species. However, there is an underlying general similarity between the two enzymes: the catalytic reaction they carry out, their cofactor requirements, and a recognition signal (albeit differing in sequence) in the −1 to −20 propeptide region. It will be important to purify the Conus enzyme and characterize it to determine the relationship between the two enzymes.

The −20 to −1 amino acid sequence of the prepropeptide is highly conserved among the conantokins. This region therefore can be used to prepare an affinity column to purify the carboxylase which post-translationally modifies Glu to γ-carboxyglutamate. Once the carboxylase is purified, it can be sequenced and cloned.

The activity of the Conus γ-glutamyl carboxylase can be assayed by contacting the carboxylase with a peptide substrate and determining the carboxylated residues in the peptide substrate. The peptide substrate comprising a first segment having an amino acid sequence of $GX_1DRLTQMKRILKKRGNX_2AR$ (SEQ ID NO:28) and a second segment which is a conantokin peptide. $X_1$ is selected from the group consisting of K, G, N and R and $X_2$ is selected from the group consisting of K, N, T and M.

EXAMPLES

The present invention is described by reference to the following Examples, which are offered by way of illustration and are not intended to limit the invention in any master. Standard techniques well known in the art or the techniques specifically described below were utilized.

Example 1

Carboxylase Assay

*Conus radiatus* venom ducts were obtained from the Philippines. Vitamin K (phytonadione) was from Abbott Laboratories, and $NaH^{14}CO_3$ 55 mCi/mmol from NEN Life Science Products. Bovine microsomes were a gift from Dr. D. W. Stafford (University of North Carolina, Chapel Hill, N.C.).

Conus microsome preparation from frozen venom ducts of *C. radiatus* was performed as described by Stanley et al.

(11). Carboxylase assay using 1 μg of Conus microsomal protein per assay was performed as follows: Conus microsomes were solubilized in 0.7% CHAPS/0.7% phosphatidyl choline/1.5 M NaCl for 20 min on ice. CHAPS is 3-[(3-cholamidopropyl)dimethyl-ammonio]-1-propanesulfonic acid. Final reactions were done in a total volume of 125 μl containing solubilized microsomes and a final concentration of reagents as follows: 25 mM MOPS (MOPS is 3-N-morpholinopropanesulfonic acid), pH 7.4, 0.5 M NaCl, 0.2% CHAPS, 0.2% phosphatidyl choline, 0.8 M ammonium sulfate, 5 μCi of NaH$^{14}$CO$_3$, 6 mM dithiothreitol (DTT), 222 μM reduced vitamin K (prepared as described by Ref. 12). Substrate and inhibitor concentrations are indicated in the legends to the figures and tables. For experiments with bovine microsomes, 380 μg of microsomal protein was present in each reaction. Reaction mixtures were incubated at 25° C. for 30 min and were quenched by the addition of 75 μl of 1N NaOH. 160 μl of the quenched reaction mixture was transferred to 1 ml of 5% trichloroacetic acid and boiled to remove unincorporated $^{14}$CO$_2$. After cooling, 5 ml of Ecolite (NEN life Science Products) was added, and the $^{14}$CO$_2$ incorporated was determined in a Beckman LS 9800 counter. The amount of microsomal proteins present in the various experiments are reported in the following Examples. All reported values are averages of three independent determinations.

Example 2

Peptide Synthesis

Peptides were synthesized on a 357ACT peptide synthesizer (Advanced ChemTech) using Fmoc (N-(9-fluorenyl) methoxycarbonyl) chemistry strategy. The peptides were cleaved from the solid support by treatment with trifluoroacetic acid/phenol/ethanedithiol/thioanisole (90/5/2.5/2.5 by volume) and purified by reverse-phase high pressure liquid chromatography (HPLC). The integrity of the peptides was verified by electrospray mass spectroscopy. Experiments were done in triplicate, and the data were analyzed using Graph Pad Prism from GraphPad Software, Inc. (San Diego, Calif.).

Example 3

Isolation of Conantokin-G cDNA

Isolation of conantokin-G cDNA was as follows. A cDNA library from *C. geographus,* in a pUC plasmid derivative, was plated out in duplicate and probed with end-labeled degenerate oligonucleotides corresponding to the mature toxin sequences. Hybridization was done in 3 M tetramethyl ammonium chloride (TMAC) (Aldrich Chemical Co, WI), 0.1 M Na$_2$HPO$_4$, 0.001 M EDTA, 5× Denhardt's solution, 0.6% SDS, 100 μg/ml sheared salmon sperm DNA, for 24 hours at 48° C. Washes were done at room temperature in 3 M TMAC, 0.05 M Tris-HCl, pH 8, 0.2% SDS for 15 min and one hour at 50° C. in a solution of the same composition. The filters were washed twice in 2×SSC, 0.1% SDS at room temperature for 15 min each. The filters were then exposed to X-ray films. Double-stranded DNA from purified clones was sequenced by dideoxynucleotide chain terminating method (13).

Example 4

Characterization of the conantokin-G Precursor

Figure 1B:
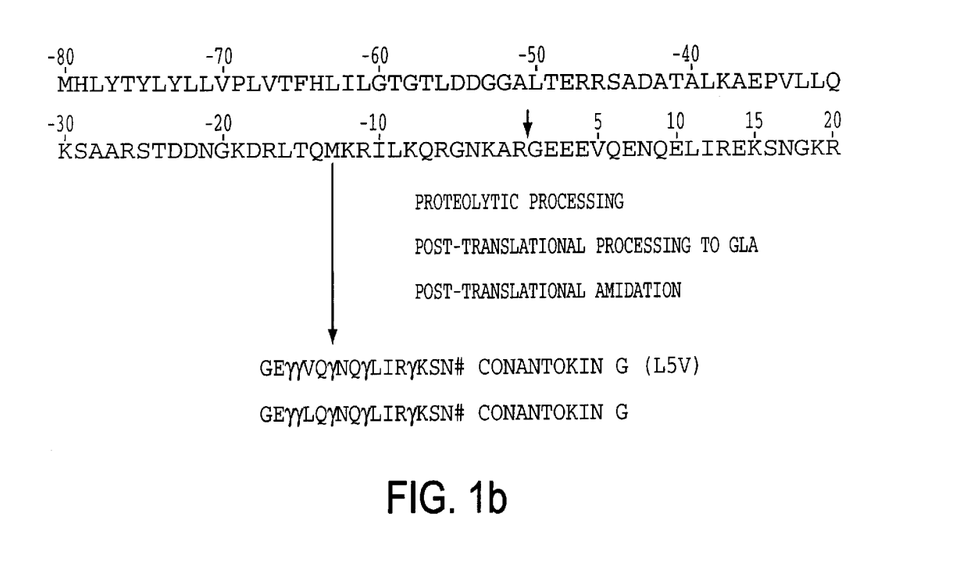

A cDNA clone encoding conantokin-G was obtained as described in Example 3. The clone was sequenced in both strands, and the nucleotide sequence obtained is shown in FIG. 1. The predicted amino acid sequence of the open reading frame encoded by this cDNA clone and the post-translational modifications that take place to yield the mature peptide are also indicated in the figure. The cDNA sequence predicts the presence of a valine residue at position 5 of the mature conantokin-G sequence. However, active peptides isolated from the venom contain leucine at this position. Using oligonucleotides corresponding to the 5' and 3' sequences of the cDNA as primers, we have also isolated the leucine containing cDNA by polymerase chain reaction (PCR) amplification of total venom duct cDNA. We have used leucine containing conantokin-G peptides in our experiments.

The sequencing data reveal that the conantokin-G precursor is generally organized in a typical Conus prepropeptide motif, with the mature peptide encoded at the C-terminal end. As expected, all γ-carboxyglutamate residues are encoded by the codons for glutamate. At the C-terminal end of the predicted open reading frame are codons encoding -Asn-Gly-Lys-Arg- Stop (SEQ ID NO:9), which signals processing to a C-terminal Asn-NH$_2$.

Immediately adjacent to Gly$^1$ of the mature conantokin-G is a typical proteolytic signal (Ala-Arg) for Conus prepropeptides. Proteolysis after the Arg residue would excise the N-terminal prepro-region of 80 amino acids containing a signal sequence of 21 amino acids at the N terminus. (However, at this point, we do not know the order of cleavage of the signal sequence and propeptide sequences.) In contrast to previously described signal sequences for conotoxins, the signal sequence for the conantokin-G precursor lacks a Cys residue (14).

A noteworthy feature of the prepropeptide is the relatively long intervening pro-region (59 amino acids). Among precursors of small Conus peptides (under 30 amino acids in length) sequenced to date, this is the longest pro-region that has been characterized so far. As we establish below, this 59-amino acid pro-region contains a γ-carboxylation recognition sequence (γ-CRS) that presumably plays a critical role in the conversion of Glu to Gla.

Example 5

Identification of γ-Carboxylation Recognition Sequence of Conantokin-G

In the case of mammalian proteins that undergo γ-carboxylation, the γ-CRS is contained in an 18-amino acid sequence (16-amino acid sequence in the case of bone peptides) immediately N-terminal to the mature peptide sequence (15–17). We investigated the ability of peptides shown in Table II to serve as substrates or affect the activity of the Conus carboxylase.

TABLE II

Primary Sequence and Apparent $K_m/IC_{50}$ of Peptides Used in This Study

| | | | SEQ ID | $K_m/IC_{50}$ ($\mu$M) |
|---|---|---|---|---|
| 1 | FLEEL | FLEEL | 10 | 301 ± 6 |
| 2 | (E.Con-G) | GEEELQENQELIREKSN-NH$_2$ | 11 | 3400 ± 215 |
| 3 | (-10.Pro-E.Con-G) | ILKQRGNKARGEEELQENQELIREKSN-NH$_2$ | 12 | 1836 ± 109 |
| 4 | (-20.Pro-E.Con-G) | GKDRLTQMKRILKQRGNKARGEEELQENQELIREKSN-NH$_2$ | 13 | 28 ± 3 |
| 5 | (-20.Pro-FLEEL) | GKDRLTQMKRILKQRGNKARFLEEL-NH$_2$ | 14 | 4 ± 0.3 |
| 6 | Pro (-20 to -1) | GKDRLTQMKRILKQRGNKAR | 15 | 490 ± 30* |
| 7 | Pro (-30 to -1) | KSAARSTDDNGKDRLTQMKRILKQRGNKAR | 16 | 200 ± 50* |
| 8 | Pro (-40 to -21) | ALKAEPVLLQKSAARSTDDN | 17 | >1000** |
| 9 | Pro (-60 to -41) | GTGTLDDGGALTERRSADAT | 18 | >1000** |

*Represents apparent $IC_{50}$ values. For experiments 6–9, carboxylation reactions were carried out using a 50 $\mu$M concentration of -20.Pro-E.Con-G and varying concentrations of competing peptide. The results were fitted to a single site competition model.
**No effects of these peptides were observed in the carboxylation reaction at a concentration of 1 mM.

Figure 2A:
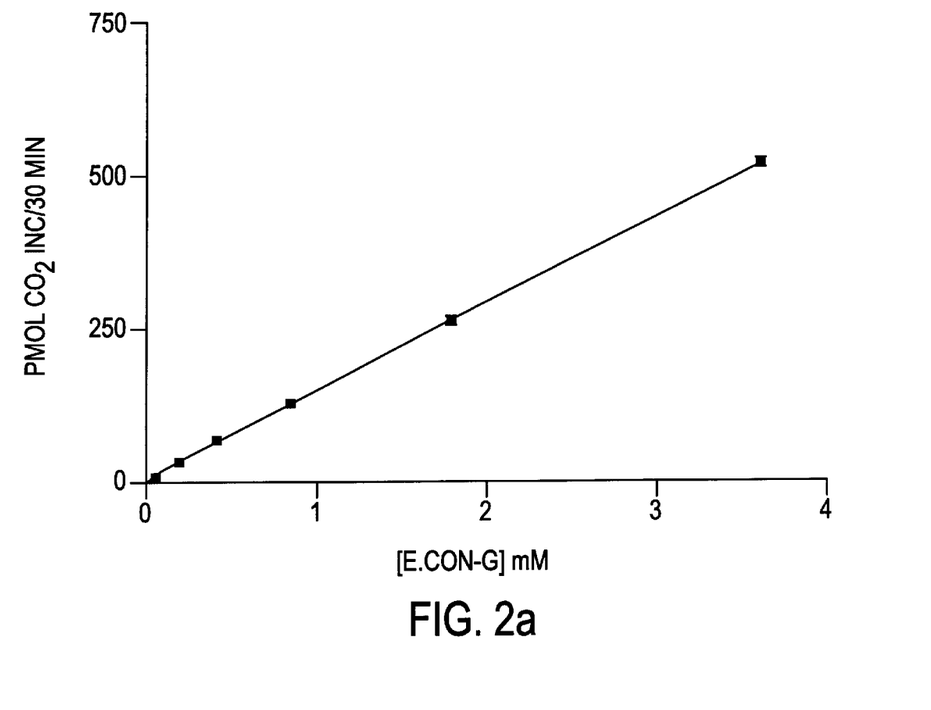
Figure 2B:
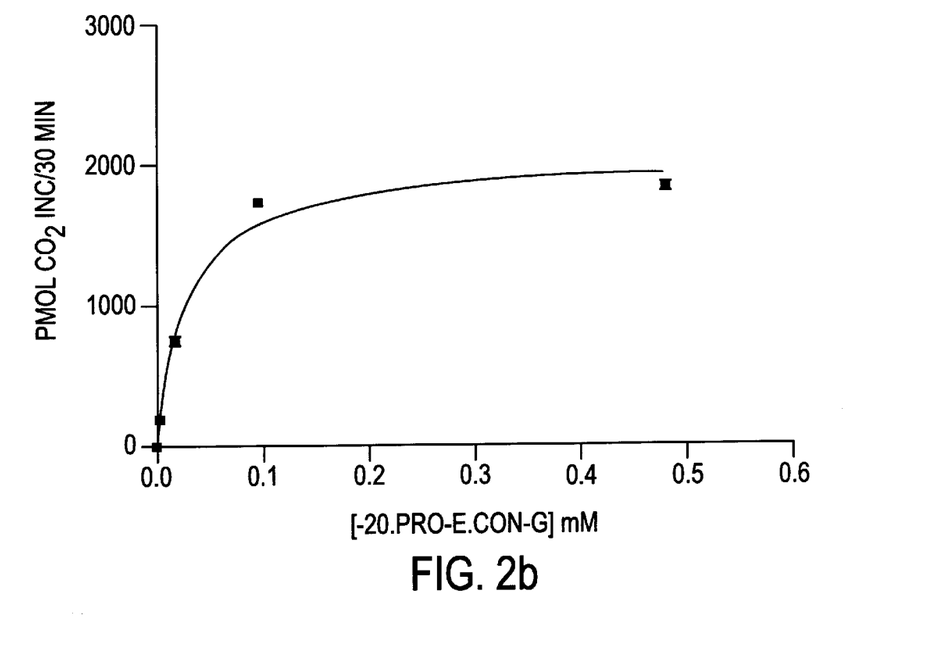

The concentration dependence for the carboxylation of peptides 1 and 3 (Table II) are shown in FIG. 2. The apparent $K_m$ for E.Con-G is 3400±215 $\mu$M and that for -20.Pro-E.Con-G. is 28±3 $\mu$M. The results clearly indicate that covalent linkage of the propeptide sequence -20 to -1 makes E.Con-G into an efficient substrate (note that the -20 to -1 sequence has no Glu residues that would be substrates for carboxylation). Similar observations were made when the -20 to -1 peptide was covalently linked to FLEEL (see Table II). The apparent $K_m$ for peptide 3 is less than that of peptide 2, suggesting that propeptide sequences between -20 and -11 also interact with the carboxylase (Table II).

We then investigated the effect of the addition of Pro(-20 to -1) in trans, on the carboxylation of FLEEL, E.Con-G, -10.Pro-E.Con-G, and -20.Pro-E.Con-G. We also determined the effect of the addition of Pro(-20 to -11) and Pro(-11 to -1) on the carboxylation of -10.Pro-E.Con-G.

Inspection of the $K_m$ values in Table II clearly indicates that substrates in which the propeptide sequences -20 to -1 are covalently linked to the N-terminus are efficient substrates for carboxylation. In the case of both E.Con-G and FLEEL, the $K_m$ decreases by two orders of magnitude. Pro(-20 to -1) stimulates the carboxylation of both FLEEL and E.Con-G when added in trans, but the effects are quite small: ~25% enhancement in the case of E.Con-G and 40% for FLEEL. Pro(-40 to -21) and Pro(-60 to -41) have no effect on the carboxylation of FLEEL or E.ConG (data not shown).

Figure 3:
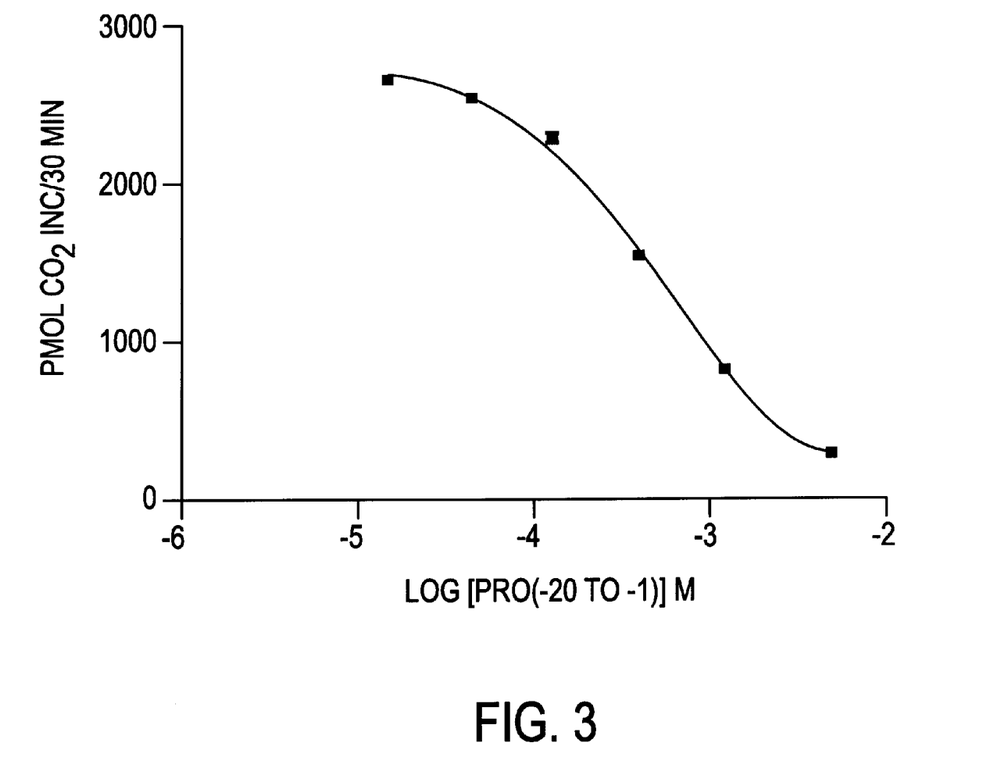

Propeptide sequence -20 to -1 is an inhibitor for the carboxylation of -10.Pro-E.Con-G (FIG. 3 and Table II) and -20.Pro-E.Con-G. The $IC_{50}$ of Pro(-20 to -1) is very similar to Pro(-30 to -1), suggesting that the interaction of the propeptide with the carboxylase in the region between -30 and -1 is probably limited to -20 to -1. Pro(-40 to -21) and Pro(-60 to -41) did not inhibit carboxylation of -10.Pro-E.Con-G even at concentrations 100-fold greater.

We also investigated the effect of alanine substitutions of the basic amino acids in the propeptide. $^{-20}$GKDRLTQMKRILKQRGNKAR$^{-1}$-GEEELY-NH$_2$(SEQ ID NO:19), a 26-amino acid peptide containing propeptide sequences -20 to -1 of conantokin-G, was used as the wild type substrate. Individual peptides, in which KR at positions -12 and -11, KQR at positions -8, -7 and -6, NK at positions -4 and -3, and NK-R at positions -4, -3 and -1 were substituted by alanine, were used as substrates in the carboxylation reaction. Carboxylation reactions were done at a substrate concentration of 40 $\mu$M, the apparent $K_m$ of carboxylation for the wild type substrate. Alanine substitutions in the context of the remaining propeptide sequences had little effect (<10%) on carboxylation.

We examined the ability of bovine microsomes to use -20.Pro-E.Con-G as substrate for γ-carboxylation. As shown in Table III, although this peptide is an excellent substrate for the Conus enzyme, it is extremely poor for the mammalian enzyme.

TABLE III

Carboxylation by Bovine and Conus Microsomes

| Additions | pmol $^{14}CO_2$ Incorporated |
|---|---|
| Bovine Microsomes | |
| Endogenous | 1 |
| FLEEL (1.2 mM) | 249 |
| -20.Pro-E.Con-G (0.28 mM) | 3 |
| Conus Microsomes | |
| Endogenous | 11 |
| FLEEL (1.2 mM) | 818 |
| -20.Pro-E.Con-G (0.28 mM) | 2741 |

Example 6

Purification of Carboxylase by an Affinity Column

As shown in Example 5, the -20 to -1 pro-region interacts with the carboxylase. This region therefore can be used as an affinity probe to purify the carboxylase. The -20 to -1 region is highly conserved among the conantokins. Sequences of the -20 to -1 propeptide region of several conantokins are shown in Table IV. These sequences are set forth in PCT/US97/12618 (U.S. Ser. No. 09/142,080) which is incorporated herein by reference.

By attaching a peptide comprising the -20 to -1 region of a conantokin to a column or to a substrate to be used as a batch affinity method, a carboxylase which carboxylates Glu to γ-carboxyglutamate can be isolated. Standard protein purification techniques known to those of ordinary skill in the art can be utilized to aid in the purification of such a carboxylase, with the affinity step being a critical step in purifying the carboxylase. The purification steps can be monitored by using a carboxylase assay as detailed in Example 1.

TABLE IV

−20 to −1 Conantokin Propeptide Sequences

| Conantokin | Sequence | SEQ ID NO: |
|---|---|---|
| ConG | GKDRLTQMKRILKQRGNKAR | 20 |
| ConOc | GGDRLTQMKRILKKRGNKAR | 21 |
| ConR | GNDRLTQMKRILKKRGNKAR | 22 |
| ConSl | GKDRLTQMKRILKKRGKNAR | 23 |
| ConL | GNDRLTQMKRILKKRGNKAR | 24 |
| ConGm | GKDRMTQRKRILKKRGNTAR | 25 |
| ConCa2 | GKDRLTQRKRTLKKRGNMAR | 26 |
| ConQu | DRDRLTQMKRILKKRGNTAR | 27 |
| Consensus | $GX_1DRLTQMKRILKKRGNX_2AR$ | 28 |

$X_1$ represents Lys, Gly, Asn or Arg; $X_2$ represents Lys, Asn, Thr or Met.

Example 7

Identification of Gla Residues

In order to ascertain the fidelity of γ-carboxylation, it is essential to determine if the appropriate Glu residues are being modified and if the modification goes to completion. We used ConG and −20.pro.ConG as substrates to determine fidelity of carboxylation. The identification of Gla by routine amino acid sequencing is not efficient due to poor recovery of Gla residues. In the present modified method, Gla-containing peptides are decarboxylated by heating under vacuum. The Gla residues are converted to Glu which can then be sequenced. If $^{14}CO_2$ is incorporated in the γ-carboxylation reaction, half of the molecules in the decarboxylated product will contain $^{14}CO_2$ covalently linked to the γ-C of modified Glu residues. Thus, by monitoring the radioactivity recovered at each step of the sequencing reaction, the position of Gla residues can be determined.

Products of the γ-carboxylation reaction was purified using a Waters Oasis™ HLB Extraction Cartridge followed by reversed phase HPLC using Vydac $C_{18}$ column. The [$^{14}C$]-containing fractions were dried and sequenced chemically with concomitant determination of radioactivity at each position in the sequence. When −20.pro.ConG was used as the substrate, the radioactivity-containing fraction from the reversed phase HPLC column was dried and digested with endoproteinase Lys C. This was done to reduce the length of the peptide for sequencing without interfering with the identification of the γ-carboxylated residues. The Lys C digest was purified using a Waters Oasis™ HLB Extraction Cartridge followed by reversed phase HPLC using Vydac $C_{18}$ column. The radioactivity eluted as a single peak coincidental with the $A_{220}$ peak. The chemical sequence of the material had the expected sequence.

Figure 4:
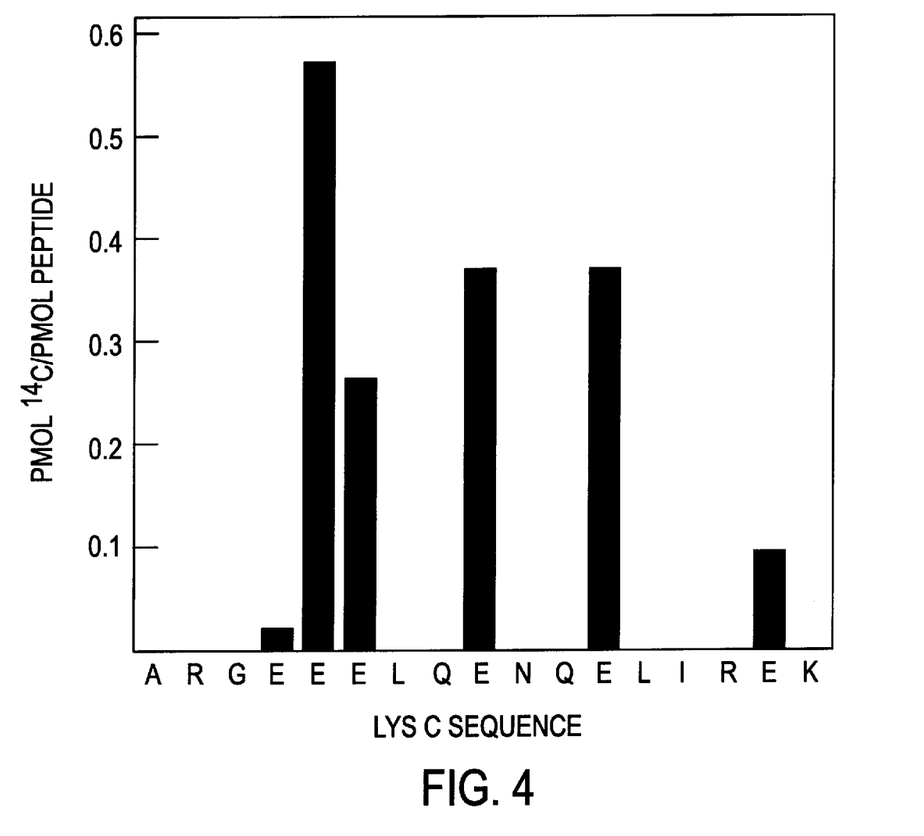

The Gla determinations were carried out on a mixture of unmodified and variously modified substrate molecules. On the basis of these experiments, it was not possible to assign Gla residues to individual post-translationally modified substrate molecules. However, an average picture emerged as shown in FIG. 4. As in the case of the native product, $Glu_2$ was not carboxylated. The rest of the Glu residues were carboxylated, although $Glu_{14}$ was not efficiently carboxylated.

Once a carboxylase is purified, its amino acid sequence can be determined by standard techniques. Knowledge of the amino acid sequence will then allow one to screen DNA libraries to obtain the gene or cDNA encoding the carboxylase. The cloned gene or cDNA can be used for a variety of purposes, e.g., producing carboxylase via in vitro translation systems, modifying the DNA sequence to produce modified forms of carboxylase enzyme, etc.

The γ-carboxylated 17-amino acid Conus peptide conantokin-G is initially translated as a prepropeptide of 100 amino acids. The precursor is similar to that previously reported for disulfide-rich conotoxins. The mature peptide is found in a single copy at the C-terminal end of the precursor and is processed post-translationally producing: γ-carboxylation of five Glu residues, C-terminal amidation of $Asn_{17}$ following excision of the C-terminal tripeptide, and a proteolytic event between $Arg_{-1}$ and $Gly_1$. The conantokin-G precursor has 59 amino acids in the intervening pro-region, the longest so far reported for any Conus venom peptide with a potential function of a γ-carboxylation recognition sequence for the Conus venom duct g-glutamyl carboxylase in the −1 to −20 region. The γ-carboxylation recognition sequence included in the −1 to −20 region of the conantokin-G prepropeptide appears to increase the affinity of the Conus carboxylase by approximately 2 orders of magnitude. As shown herein, the Conus γ-carboxylase correctly carboxylates conantokin G, i.e., the same 5 of the 6 Glu residues are carboxylated in vitro as occurs in vivo.

It will be appreciated that the methods and compositions of the instant invention can be incorporated in the form of a variety of embodiments, only a few of which are disclosed herein. It will be apparent to the artisan that other embodiments exist and do not depart from the spirit of the invention. Thus, the described embodiments are illustrative and should not be construed as restrictive.

LIST OF REFERENCES

1. Stenflo, J., Fernlund, P., Egan, W. and Roepstorff, P. (1974). *Proc. Natl. Acid. Sci. USA* 71: 2730–2733.
2. Price, P. A. and Williamson, M. K. (1985). *J. Biol. Chem.* 260: 14971–14975.
3 McIntosh, J. M., Olivera, B. M., Cruz, L. J. and Gray, W. R. (1984). *J. Biol. Chem.* 259: 14343–14346.
4. Olivera, B. M., Rivier, J., Clark, C., Ramilo, C. A., Corpuz, G. P., Abogadie, F. C., Mena, E. E., Woodward, S. R., Hillyard, D. R. and Cruz, L. J. (1990). *Science* 249: 257–263.
5. Haack, J. A., Rivier, J., Parks, T. N., Mena, E. E., Cruz, L. J. and Olivera, B. M. (1990). *J. Biol. Chem.* 265: 6025–6029.
6. White, H. S., McCabe, R. T., Abogadie, F., Torres, J., Rivier, J. E., Paarmann, I., Hollmann, M., Olivera, B. M. and Cruz, L. J. (1997). *J. Neurosci.* Abst.
7. Wu, S.-M., Morris, D. P. and Stafford, D. W. (1991). *Proc. Natl. Acad. Sci. USA* 88: 2236–2240.
8. Berkner, K. L., Harbeck, M., Lingenfelter, S., Bailey, C., Sanders-Hinck, C. M. and Suttie, J. W. (1992). *Proc. Natl. Acad. Sci. USA* 89: 6242–6246.

9. Wu, S.-M., Cheung, W.-F., Frazier, D. and Stafford, D. W. (1991). *Science* 254: 1634–1636.
10. Roth, D. A., Rehemtulla, A., Kaufman, R. H., Walsh, C. T., Furie, B. and Furie, B. C. (1993). *Proc. Natl. Acad. Sci. USA* 90: 8372–8376.
11. Stanley, T. B., Stafford, D. W., Olivera, B. M. and Bandyopadhyay, P. K. (1997). *FEBS Lett.* 407: 85–88.
12. Buitenhuis, H. C., Soute, B. A. M. and Vermeer, C. (1990). *Biochim. Biophys. Acta* 1034: 170–175.
13. Sanger, F., Nicklen, S. and Coulson, A. R. (1977). *Proc. Natl. Acad. Sci. USA* 74: 5463–5467.
14. Colledge, C. J., Hunsperger, J. P., Imperial, J. S. and Hillyard, D. R. (1992). *Toxicon* 30: 1111–1116.
15. Pan, L. C. and Price, P. A. (1985). *Proc. Natl. Acad. Sci. USA* 82: 6109–6113.
16. Price, P. A., Fraser, J. D. and Metz-Virca, G. (1987). *Proc. Natl. Acad. Sci. USA* 84: 8335–8339.
17. Kuliopulos, A., Cieurzo, C. E., Furie, B., Furie, B. C. and Walsh, C. T. (1992). *Biochemistry* 31: 9436–9444.
18. Knobloch, J. E. and Suttie, J. W. (1987). *J. Biol. Chem.* 262: 15334–15337.
19. Cheung, A., Engelke, J. A., Sanders, C. and Suttie, J. W. (1989). *Arch. Biochem. Biophys.* 274: 574–581.
20. Ulrich, M. M. W., Furie, B., Jacobs, M. R., Vermeer, C. and Furie, B. C. (1988). *J. Biol. Chem.* 263: 9697–9702.
21. Kurachi, K. and Davie, E. W. (1982). *Proc. Natl. Acad. Sci. USA* 79: 6461–6464.
22. Fung, M. R., Hay, C. W. and MacGillivray, R. T. A. (1985). *Proc. Natl. Acad. Sci. USA* 82: 3591–3595.
23. Friezner Degan, S. J., MacGillivray, R. T. A. and Davie, E. W. (1983). *Biochemistry* 22: 2087–2097.
24. Skjaebaek, N., Nielsen, K. J., Lewis, R. J., Alewood, P. and Craik, D. J. (1997). *J. Biol. Chem.* 272: 2291–2299.
25. Warder, S. E., Chen, Z., Zhu, Y., Prorok, M., Castellino, F. J. and Ni, F. (1997). *FEBS Lett.* 411: 19–26.
26. Rigby, A. C., Baleja, J. D., Furie, B. C. and Furie, B. (1997). *Biochemistry* 36: 6906–6914.

What is claimed is:

1. A method for purifying a Conus γ-glutamyl carboxylase wherein said method comprises binding said carboxylase to a peptide using affinity chromatrography and isolating said carboxylase, wherein said peptide comprises region −20 to −1 of a conantokin propeptide.

2. The method of claim 1 wherein said peptide is a conantokin propeptide.

3. The method of claim 1, wherein during said affinity chromatography said peptide is attached to a column.

4. The method of claim 1 wherein said conantokin propeptide region has an amino acid sequence of $GX_1DRLTQMKRILKKRGNX_2AR$ (SEQ ID NO:28), wherein $X_1$ is selected from the group consisting of K, G, N and R and $X_2$ is selected from the group consisting of K, N, T and M.

5. A method for assaying a Conus γ-glutamyl carboxylase wherein said method comprises contacting said carboxylase with a peptide substrate and determining the carboxylated residues in the peptide substrate, said peptide substrate comprising a first segment having an amino acid sequence of $GX_1DRLTQMKRILKKRGNX_2AR$ (SEQ ID NO:28) and a second segment which is a conantokin peptide, wherein $X_1$ is selected from the group consisting of K, G, N and R and $X_2$ is selected from the group consisting of K, N, T and M.

6. The method of claim 5, wherein said conantokin peptide is conantokin G.

7. The method of claim 6, wherein said conantokin G has the amino acid sequence set forth in SEQ ID NO:4.

* * * * *

SEQUENCE LISTING

<160> NUMBER OF SEQ ID NOS: 28

<210> SEQ ID NO 1
<211> LENGTH: 303
<212> TYPE: DNA
<213> ORGANISM: Conus geographus
<220> FEATURE:
<221> NAME/KEY: CDS
<222> LOCATION: (1)..(300)

<400> SEQUENCE: 1

```
atg cac ctg tac acg tat ctg tat ctg ctg gtg ccc ctg gtg acc ttc      48
Met His Leu Tyr Thr Tyr Leu Tyr Leu Leu Val Pro Leu Val Thr Phe
 1               5                  10                  15 cac cta atc cta ggc acg ggc aca cta gat gat gga ggc gca ctg act      96
His Leu Ile Leu Gly Thr Gly Thr Leu Asp Asp Gly Gly Ala Leu Thr
             20                  25                  30 gaa cgc cgt tca gct gac gcc act gcg ctg aaa gct gag cct gtc ctc     144
Glu Arg Arg Ser Ala Asp Ala Thr Ala Leu Lys Ala Glu Pro Val Leu
         35                  40                  45 ctg cag aaa tcc gct gcc cgc agc acc gac gac aat ggc aag gac agg     192
Leu Gln Lys Ser Ala Ala Arg Ser Thr Asp Asp Asn Gly Lys Asp Arg
     50                  55                  60 ttg act cag atg aag agg att ctc aaa cag cga gga aac aaa gcc aga     240
Leu Thr Gln Met Lys Arg Ile Leu Lys Gln Arg Gly Asn Lys Ala Arg
 65                  70                  75                  80 ggc gaa gaa gaa gtt caa gag aat cag gaa ttg atc aga gaa aaa agt     288
Gly Glu Glu Glu Val Gln Glu Asn Gln Glu Leu Ile Arg Glu Lys Ser
                 85                  90                  95 aat gga aaa aga taa                                                  303
Asn Gly Lys Arg
            100
```

<210> SEQ ID NO 2
<211> LENGTH: 100
<212> TYPE: PRT
<213> ORGANISM: Conus geographus

<400> SEQUENCE: 2

```
Met His Leu Tyr Thr Tyr Leu Tyr Leu Leu Val Pro Leu Val Thr Phe
 1               5                  10                  15
```

```
His Leu Ile Leu Gly Thr Gly Thr Leu Asp Asp Gly Gly Ala Leu Thr
            20                  25                  30

Glu Arg Arg Ser Ala Asp Ala Thr Ala Leu Lys Ala Glu Pro Val Leu
        35                  40                  45

Leu Gln Lys Ser Ala Ala Arg Ser Thr Asp Asp Asn Gly Lys Asp Arg
    50                  55                  60

Leu Thr Gln Met Lys Arg Ile Leu Lys Gln Arg Gly Asn Lys Ala Arg
65                  70                  75                  80

Gly Glu Glu Val Gln Glu Asn Gln Glu Leu Ile Arg Glu Lys Ser
                85                  90                  95

Asn Gly Lys Arg
            100

<210> SEQ ID NO 3
<211> LENGTH: 17
<212> TYPE: PRT
<213> ORGANISM: Conus geographus
<220> FEATURE:
<221> NAME/KEY: PEPTIDE
<222> LOCATION: (3)..(14)
<223> OTHER INFORMATION: Xaa is gamma-carboxy-Glu

<400> SEQUENCE: 3

Gly Glu Xaa Xaa Val Gln Xaa Asn Gln Xaa Leu Ile Arg Xaa Lys Ser
1               5                   10                  15

Asn

<210> SEQ ID NO 4
<211> LENGTH: 17
<212> TYPE: PRT
<213> ORGANISM: Conus geographus
<220> FEATURE:
<221> NAME/KEY: PEPTIDE
<222> LOCATION: (3)..(14)
<223> OTHER INFORMATION: Xaa is gamma-carboxy-Glu

<400> SEQUENCE: 4

Gly Glu Xaa Xaa Leu Gln Xaa Asn Gln Xaa Leu Ile Arg Xaa Lys Ser
1               5                   10                  15

Asn

<210> SEQ ID NO 5
<211> LENGTH: 20
<212> TYPE: PRT
<213> ORGANISM: Conus geographus

<400> SEQUENCE: 5

Gly Lys Asp Arg Leu Thr Gln Met Lys Arg Ile Leu Lys Gln Arg Gly
1               5                   10                  15

Asn Lys Ala Arg
            20

<210> SEQ ID NO 6
<211> LENGTH: 18
<212> TYPE: PRT
<213> ORGANISM: Homo sapiens

<400> SEQUENCE: 6

Thr Val Phe Leu Asp His Glu Asn Ala Asn Lys Ile Leu Asn Arg Pro
1               5                   10                  15

Leu Arg
```

```
<210> SEQ ID NO 7
<211> LENGTH: 18
<212> TYPE: PRT
<213> ORGANISM: Homo sapiens

<400> SEQUENCE: 7

Ser Leu Phe Ile Arg Arg Glu Gln Ala Asn Asn Ile Leu Ala Arg Val
 1               5                  10                  15
Thr Arg

<210> SEQ ID NO 8
<211> LENGTH: 18
<212> TYPE: PRT
<213> ORGANISM: Homo sapiens

<400> SEQUENCE: 8

His Val Phe Leu Ala Pro Gln Gln Ala Arg Ser Leu Leu Gln Arg Val
 1               5                  10                  15
Arg Arg

<210> SEQ ID NO 9
<211> LENGTH: 4
<212> TYPE: PRT
<213> ORGANISM: Conus geographus

<400> SEQUENCE: 9

Asn Gly Lys Arg
 1

<210> SEQ ID NO 10
<211> LENGTH: 5
<212> TYPE: PRT
<213> ORGANISM: Artificial Sequence
<220> FEATURE:
<223> OTHER INFORMATION: Description of Artificial Sequence:test peptide

<400> SEQUENCE: 10

Phe Leu Glu Glu Leu
 1               5

<210> SEQ ID NO 11
<211> LENGTH: 17
<212> TYPE: PRT
<213> ORGANISM: Conus geographus

<400> SEQUENCE: 11

Gly Glu Glu Glu Leu Gln Glu Asn Gln Glu Leu Ile Arg Glu Lys Ser
 1               5                  10                  15
Asn

<210> SEQ ID NO 12
<211> LENGTH: 27
<212> TYPE: PRT
<213> ORGANISM: Conus geographus

<400> SEQUENCE: 12

Ile Leu Lys Gln Arg Gly Asn Lys Ala Arg Gly Glu Glu Glu Leu Gln
 1               5                  10                  15
Glu Asn Gln Glu Leu Ile Arg Glu Lys Ser Asn
                20                  25

<210> SEQ ID NO 13
```

```
<211> LENGTH: 37
<212> TYPE: PRT
<213> ORGANISM: Conus geographus

<400> SEQUENCE: 13

Gly Lys Asp Arg Leu Thr Gln Met Lys Arg Ile Leu Lys Gln Arg Gly
  1               5                  10                  15

Asn Lys Ala Arg Gly Glu Glu Glu Leu Gln Glu Asn Gln Glu Leu Ile
             20                  25                  30

Arg Glu Lys Ser Asn
         35

<210> SEQ ID NO 14
<211> LENGTH: 25
<212> TYPE: PRT
<213> ORGANISM: Artificial Sequence
<220> FEATURE:
<223> OTHER INFORMATION: Description of Artificial Sequence:pro-test
      peptide

<400> SEQUENCE: 14

Gly Lys Asp Arg Leu Thr Gln Met Lys Arg Ile Leu Lys Gln Arg Gly
  1               5                  10                  15

Asn Lys Ala Arg Phe Leu Glu Glu Leu
             20                  25

<210> SEQ ID NO 15
<211> LENGTH: 20
<212> TYPE: PRT
<213> ORGANISM: Conus geographus

<400> SEQUENCE: 15

Gly Lys Asp Arg Leu Thr Gln Met Lys Arg Ile Leu Lys Gln Arg Gly
  1               5                  10                  15

Asn Lys Ala Arg
             20

<210> SEQ ID NO 16
<211> LENGTH: 30
<212> TYPE: PRT
<213> ORGANISM: Conus geographus

<400> SEQUENCE: 16

Lys Ser Ala Ala Arg Ser Thr Asp Asp Asn Gly Lys Asp Arg Leu Thr
  1               5                  10                  15

Gln Met Lys Arg Ile Leu Lys Gln Arg Gly Asn Lys Ala Arg
             20                  25                  30

<210> SEQ ID NO 17
<211> LENGTH: 20
<212> TYPE: PRT
<213> ORGANISM: Conus geographus

<400> SEQUENCE: 17

Ala Leu Lys Ala Glu Pro Val Leu Leu Gln Lys Ser Ala Ala Arg Ser
  1               5                  10                  15

Thr Asp Asp Asn
         20

<210> SEQ ID NO 18
<211> LENGTH: 20
<212> TYPE: PRT
<213> ORGANISM: Conus geographus
```

```
<400> SEQUENCE: 18

Gly Thr Gly Thr Leu Asp Asp Gly Gly Ala Leu Thr Glu Arg Arg Ser
 1               5                  10                  15

Ala Asp Ala Thr
            20

<210> SEQ ID NO 19
<211> LENGTH: 26
<212> TYPE: PRT
<213> ORGANISM: Conus geographus

<400> SEQUENCE: 19

Gly Lys Asp Arg Leu Thr Gln Met Lys Arg Ile Leu Lys Gln Arg Gly
 1               5                  10                  15

Asn Leu Ala Arg Gly Glu Glu Glu Leu Tyr
            20                  25

<210> SEQ ID NO 20
<211> LENGTH: 20
<212> TYPE: PRT
<213> ORGANISM: Conus geographus

<400> SEQUENCE: 20

Gly Lys Asp Arg Leu Thr Gln Met Lys Arg Ile Leu Lys Gln Arg Gly
 1               5                  10                  15

Asn Lys Ala Arg
            20

<210> SEQ ID NO 21
<211> LENGTH: 20
<212> TYPE: PRT
<213> ORGANISM: Conus ochroleucus

<400> SEQUENCE: 21

Gly Gly Asp Arg Leu Thr Gln Met Lys Arg Ile Leu Lys Lys Arg Gly
 1               5                  10                  15

Asn Lys Ala Arg
            20

<210> SEQ ID NO 22
<211> LENGTH: 20
<212> TYPE: PRT
<213> ORGANISM: Conus radiatus

<400> SEQUENCE: 22

Gly Asn Asp Arg Leu Thr Gln Met Lys Arg Ile Leu Lys Lys Arg Gly
 1               5                  10                  15

Asn Lys Ala Arg
            20

<210> SEQ ID NO 23
<211> LENGTH: 20
<212> TYPE: PRT
<213> ORGANISM: Conus sulcatus

<400> SEQUENCE: 23

Gly Lys Asp Arg Leu Thr Gln Met Lys Arg Ile Leu Lys Lys Arg Gly
 1               5                  10                  15

Lys Asn Ala Arg
            20
```

```
<210> SEQ ID NO 24
<211> LENGTH: 20
<212> TYPE: PRT
<213> ORGANISM: Conus lynceus

<400> SEQUENCE: 24

Gly Asn Asp Arg Leu Thr Gln Met Lys Arg Ile Leu Lys Lys Arg Gly
 1               5                  10                  15

Asn Lys Ala Arg
            20

<210> SEQ ID NO 25
<211> LENGTH: 20
<212> TYPE: PRT
<213> ORGANISM: Conus gloriamaris

<400> SEQUENCE: 25

Gly Lys Asp Arg Met Thr Gln Arg Lys Arg Ile Leu Lys Lys Arg Gly
 1               5                  10                  15

Asn Thr Ala Arg
            20

<210> SEQ ID NO 26
<211> LENGTH: 20
<212> TYPE: PRT
<213> ORGANISM: Conus caracteristicus

<400> SEQUENCE: 26

Gly Lys Asp Arg Leu Thr Gln Arg Lys Arg Thr Leu Lys Lys Arg Gly
 1               5                  10                  15

Asn Met Ala Arg
            20

<210> SEQ ID NO 27
<211> LENGTH: 20
<212> TYPE: PRT
<213> ORGANISM: Conus quercinus

<400> SEQUENCE: 27

Asp Arg Asp Arg Leu Thr Gln Met Lys Arg Ile Leu Lys Lys Arg Gly
 1               5                  10                  15

Asn Thr Ala Arg
            20

<210> SEQ ID NO 28
<211> LENGTH: 20
<212> TYPE: PRT
<213> ORGANISM: Artificial Sequence
<220> FEATURE:
<223> OTHER INFORMATION: Description of Artificial Sequence:consensus
      Conus propeptide sequence
<220> FEATURE:
<221> NAME/KEY: PEPTIDE
<222> LOCATION: (2)..(18)
<223> OTHER INFORMATION: Xaa at residue 2 is Lys, Gly, Asn or Arg; Xaa
      at residue 18 is Lys, Asn, Thr or Met.

<400> SEQUENCE: 28

Gly Xaa Asp Arg Leu Thr Gln Met Lys Arg Ile Leu Lys Lys Arg Gly
 1               5                  10                  15

Asn Xaa Ala Arg
            20
```